United States Patent [19]
Otte

[11] Patent Number: 4,523,960
[45] Date of Patent: Jun. 18, 1985

[54] METHOD FOR THE PRODUCTION OF HIGH FRUCTOSE CORN SYRUP

[75] Inventor: Joseph N. A. Otte, Ruisbroek, Belgium

[73] Assignee: Dow Chemical, Belgium, S.A., Midland, Mich.

[21] Appl. No.: 560,040

[22] Filed: Dec. 9, 1983

[30] Foreign Application Priority Data

Dec. 22, 1982 [EP] European Pat. Off. ......... 822016523

[51] Int. Cl.³ .............................................. C13D 3/14
[52] U.S. Cl. ................................................. 127/46.2
[58] Field of Search ....................... 127/46.2; 210/685

[56] References Cited

U.S. PATENT DOCUMENTS

| | | | |
|---|---|---|---|
| 2,753,279 | 7/1956 | Cushing et al. | 127/46.2 |
| 3,784,409 | 1/1974 | Nelson et al. | 127/46.2 |
| 3,985,648 | 10/1976 | Casolo | 210/686 |
| 4,247,340 | 1/1981 | Cartier | 127/46.2 |

Primary Examiner—Ivars Cintins

[57] ABSTRACT

The preparation of high fructose corn syrup wherein the glucose-containing process stream is sequentially contacted with a strong acid cation-exchange resin and then a weak base anion-exchange resin prior to enzyme isomerization of the glucose to fructose is facilitated by treating the process stream with a weak acid cation-exchange resin subsequent to its treatment with the strong acid and weak base resins but prior to enzyme isomerization.

8 Claims, No Drawings

METHOD FOR THE PRODUCTION OF HIGH FRUCTOSE CORN SYRUP

BACKGROUND OF THE INVENTION

The present invention relates to an improved process for the preparation of high fructose corn syrup, particularly, to an improved process for converting glucose to high fructose corn syrup using enzyme isomerization techniques.

Heretofore, corn and other vegetable starches have been converted to glucose using a strong acid such as hydrochloric acid or enzymes which catalyze the breakdown of the starch to glucose. Since the converted starches are not sufficiently sweet to compete with sucrose in many applications, a microorganism capable of producing glucose isomerase which converts glucose to the sweeter fructose has been employed. The resulting corn syrup is commonly referred to as high fructose corn syrup or simply HFCS. Methods for producing HFCS, including the often employed enrichment and polishing operations, are well-known in the art.

In conventional methods for preparing HFCS, the glucose which has been produced from the corn and/or other vegetable starch using conventional techniques is deashed and decolorized prior to actual enzyme isomerization of the glucose to a glucose/fructose mixture. Conventionally, deashing (specifically the removal of sulfate and chloride salts of calcium, magnesium and potassium) and decolorizing is achieved by sequentially treating the glucose with a strong acid, cation-exchange resin and subsequently with a weak base, anion-exchange resin. The strong acid, cation-exchange resin removes the cationic species, e.g., calcium, magnesium and potassium cations from the glucosic process stream. Alternatively, the weak base, anion-exchange resin removes the chloride and sulfate anions from the process stream. In addition, the anion-exchange resin removes significant amounts of the color bodies originally present in the corn syrup.

Subsequent to the treatment with the ion-exchange resins, the pH of the corn syrup is generally from about 8 to 10. Since an acidic pH of from about 4 to 6 is required for effective enzyme isomerization of the glucose to fructose, an acid such as HCl is added to the glucosic syrup.

The glucose is then isomerized. The resulting glucose/fructose mixture is purified by sequentially treating the mixture with a strong acid, cation-exchange resin and a strong base, anion-exchange resin and subsequently recovered using conventional techniques.

Unfortunately, in the described process, the adjustment of the pH of the glucosic syrup by adding the strong acid prior to the enzyme isomerization step introduces undesirable anionic impurities in the process stream which must be removed subsequently during the purification of the glucose/fructose mixture. In addition, the amino acids and amino acid derivatives, which acids and derivatives are commonly found in the glucosic process stream, are generally the first ionic components to leak from strong acid resin and undesirably high amounts of the acids and their derivatives are often present during the actual isomerization step.

Moreover, upon the exhaustion of the anion resin employed in the deashing/decolorization operations (i.e., the reduction in the ability of the resin to remove anions from the glucosic syrup to a commercially impractical level), the resin must subsequently be regenerated prior to its reuse. In conventional processes, the anion resin is regenerated using either a sodium carbonate, ammonium hydroxide or sodium hydroxide solution. Unfortunately, following regeneration, the resin must be thoroughly rinsed using deionized water to remove the desired amounts of sodium, ammonium and compounds thereof entrapped or otherwise entrained within the anion resin during regeneration. After multiple cycles of operation (e.g., 100 operation cycles), undesirable large amounts of rinse water, for example up to 20 to 30 resin bed volumes are required to rinse the desired amounts of sodium from the resins. Although the ammonium cations are more easily rinsed from the regenerated resin, ammonium hydroxide possesses a noxious odor and does not effectively remove trapped organic bodies from the anion-exchange resin during regeneration.

In view of the aforementioned deficiencies of the prior art in preparing HFCS, it remains highly desirable to provide an improved method for producing HFCS which does not have the aforementioned deficiencies.

SUMMARY OF THE INVENTION

Accordingly, the present invention is such an improved method for the preparation of HFCS. The method for preparing the HFCS comprises the steps of sequentially treating a glucose-containing stream with a strong acid, cation-exchange resin and then with an anion-exchange resin and thereafter converting at least a portion of the glucose to fructose using enzyme isomerization techniques. The improvement in said method comprises treating the glucose-containing process stream with a weak acid, cation-exchange resin subsequent to the sequential treatment of the process stream with the strong acid and anion resins but prior to the isomerization of glucose to fructose.

Using the method of the present invention, the addition of a strong acid such as HCl for the purposes of adjusting the pH of the process stream prior to isomerization of the glucose is eliminated. Specifically, the treatment of the process stream with the weak acid resin prior to isomerization, but subsequent to sequential treatment with the strong acid and anion resins, imparts the desirable pH to the stream for subsequent isomerization. Therefore, the problems of subsequently removing the anions (i.e., Cl$^-$) added with the acid are eliminated.

In addition, it is unnecessary to thoroughly and completely rinse the ammonium, sodium or compound thereof which have been entrained or entrapped in the anion resin during the regeneration of the exhausted resin. Specifically, the entrapped or entrained sodium or ammonium remaining in the resin following the water rinse will be rinsed from the anion resin by the glucosic process stream. In the practice of the present invention the rinsed sodium or ammonium is subsequently removed from the process stream prior to enzyme isomerization by the weak acid resin. Therefore, the amounts of rinse water necessary in washing or rinsing the regenerated resin and the time consumed in said rinse or wash are significantly reduced.

Furthermore, the amino acids and amino acid derivatives which leak from the strong acid resin are effectively removed by the weak acid resin prior to the introduction of glucosic stream to the enzyme isomerization step.

DETAILED DESCRIPTION OF THE INVENTION

In the method of the present invention, the process stream in the preparation of HFCS is contacted sequentially with a strong acid resin, an anion-exchange resin, most preferably a weak base resin, and a weak acid resin prior to the enzyme isomerization of glucose to fructose.

Weak acid, cation-exchange resins (hereinafter referred to as "weak acid resins") and methods for their preparation, including kinds of monomeric components, catalyst and polymerization media, are well-known in the art and reference is made thereto for the purposes of the present invention. In general, the weak acid resins advantageously employed in the practice of the present invention are cross-linked copolymers bearing pendent carboxyl groups.

In one method for preparing said weak acid resins, as disclosed by U.S. Pat. Nos. 2,340,110 and 2,340,111, the weak acid resins are prepared by copolymerizing an alpha,beta-ethylenically unsaturated acid such as acrylic or methacrylic acid with a cross-linking monomer. Alternatively, as described by U.S. Pat. No. 2,597,437, the weak acid resin can be prepared by copolymerizing an ester of an alpha,beta-ethylenically unsaturated acid such as ethyl methacylate or methyl acrylate with a cross-linking monomer and subsequently hydrolyzing the copolymerization product. The preferred weak acid resins are the cross-linked polymers of acrylic and/or methacrylic acid.

Representative cross-linking monomers employed in preparing the weak acid resin using either of the foregoing techniques include the polyvinylidene aromatics such as divinylbenzene, divinyl toluene, divinyl xylene, divinyl naphthalene, divinyl sulfone, trivinylbenzene or isopropenyl vinylbenzene; divinyl sulfide; ethylene glycol dimethylacryalate and the like. Of such cross-linking monomers, divinylbenzene and ethylene glycol dimethacrylate, particularly divinylbenzene, are preferably employed herein.

The weak acid resin can be prepared in the form of a macroporous (macrorecticular) type resin or gel type resin, with macroporous type resins being generally preferred. Although the resin can be prepared in granular form, preferably, the weak acid resins are prepared in the form of spheroidal beads having a volume average particle size from about 0.04 to about 2.4, preferably from 0.3 to 1.2, millimeters (mm).

The strong acid, cation-exchange resins (herein referred to as "strong acid resins") and weak base, anion-exchange resins (hereinafter referred to as "weak base resins") are well-known in the art and reference is made thereto for the purposes of this invention. In general, the strong acid and weak base resins are generally derivatives of normally solid copolymers of a monovinylidene aromatic and a cross-linking monomer copolymerizable therewith, typically a polyethylenically unsaturated monomer.

The monovinylidene aromatics and cross-linking monomers useful in the preparation of strong acid and weak base resins are well-known in the art and reference is made thereto for the purposes of this invention.

The preferred monovinylidene aromatics include styrene, halo-substituted styrenes, e.g., bromostyrene or chlorostyrene, and vinyl naphthalene. Although monoalkyl-substituted styrenes such as vinyl toluene or ethyl vinylbenzene can also be employed, especially if the substituent groups are not in a para position with respect to each other, such monoalkyl styrenes are more advantageously employed in combination with styrene. In the practice of this invention, styrene is the most preferred monovinylidene aromatic. Preferred cross-linking agents are the polyvinylidene aromatics, with divinylbenzene and divinyl sulfone, particularly divinylbenzene being the most preferred cross-linking monomer.

Although the strong acid resin can be prepared from a gel type copolymer, both the strong acid and weak base resins are preferably prepared from a macroporous (i.e., macrorecticular) type copolymer. Methods for copolymerizing the monovinylidene aromatic and cross-linking monomer (including the catalyst, polymerization media and pore forming materials) to prepare the preferred macroporous copolymers are well-known in the art and reference is made thereto for the purposes of this invention. Representative of such methods are illustrated in U.S. Pat. Nos. 3,173,892; 3,549,562; 3,637,535; and 4,104,209.

Advantageously, the cross-linked, macroporous, aromatic copolymers are prepared as spheroidal beads having a volume average particle size from 0.1 to 2.0 mm, preferably from 0.3 to 1.2 mm.

Strong acid resins are prepared from the macroporous copolymers using techniques well-known in the art for converting cross-linked copolymers of monovinylidene aromatics to a strong acid resin. Illustrative of such methods for preparing the strong base resins are U.S. Pat. Nos. 3,266,007; 2,500,149; 2,631,127; 2,664,801; and 2,764,564 (all of which are hereby incorporated by reference). In general, the strong acid resins are prepared by sulfonating the macroporous copolymer. While the sulfonation may be conducted neat, generally, the copolymers are swollen using a suitable swelling agent such as a sulfonation resistant chlorinated hydrocarbon (e.g., chlorobenzene or tetrachloroethylene) or an aliphatic or aromatic hydrocarbon (e.g., toluene or xylene) and the swollen copolymer reacted with a sulfonating agent such as sulfuric acid, chlorosulfonic acid or sulfur trioxide. Preferably, an excess amount of the sulfonating agent, e.g., from 2 to 7 times the weight of the copolymer, is employed and the sulfonation is conducted at a temperature from 50° C. to 200° C. Although the strong acid resin (and weak acid resin) employed in the practice of the present invention can be in any of a variety of cationic forms, e.g., $H^+$, $NH_4^+$, $Na^+$ or the like, the $H^+$ form of the resin generally results in the most effective operation. A preferred strong acid resin is DOWEX ® 88 (trademark of The Dow Chemical Company) cation resin available from The Dow Chemical Company.

In general, the weak base resins are generally prepared from the halomethylated product of the cross-linked addition copolymer product of the monovinylidene aromatic and cross-linking monomer. Methods of halomethylating the copolymers are well-known in the art and reference is made thereto for the purposes of the present invention. For example, as illustrated by U.S. Pat. Nos. 2,642,417; 2,960,480; 2,597,492; 2,597,493; 3,311,602; and 2,616,877, halomethylation of the cross-linked copolymer can be conducted by contacting the copolymer with a halomethylating agent such as methylamine or dimethylamine in the presence of a Friedel-Crafts catalyst. Alternatively, the halomethylated cross-linked copolymer can be prepared by copolymerizing a polymerizable halomethylated monovinylidene aromatic such as vinylbenzyl chloride with a cross-linking monomer using the well-known techniques as described in U.S. Pat. No. 2,992,544.

The weak base resins, which resins bear pendent 1°, 2° or 3° amine groups, are typically prepared by contacting a halomethylated polymer with a suitable aminating agent; generally, ammonia or a primary or secondary amine. Representative primary and secondary amines include methylamine, ethylamine, butylamine, cyclohexylamine, dimethylamine, diethylamine, and the like. Such method generally comprises heating, with reflux, a mixture of the halomethylated polymer and at least a stoichiometric amount of ammonia or the amine to a temperature sufficient to react the ammonia or amine with a benzylic halogen atom. A dispersing agent such as water, ethanol or the like is optionally employed.

Alternatively, the weak base resin can be the cross-linked addition polymerization product of a suitable nitrogen-containing compound. For example, the addition copolymerization product of vinyl pyridine or vinyl methyl pyridene; a cross-linking monomer such as divinylbenzene, divinyl ketone or methylenebisacrylamide; and, optionally, a monovinylidene aromatic such as styrene, can also be employed as the weak base resin.

The preferred weak base resins are the secondary amine derivatives of a copolymer of a styrene and divinylbenzene such as DOWEX ® 66 sold by The Dow Chemical Company.

In the practice of the present invention, the glucosic process stream is sequentially contacted with (1) a resin bed containing the strong acid resin, (2) a resin bed containing the weak base resin, and (3) a resin bed containing the weak acid resin at conditions sufficient to remove the desired amounts of the anions, cations and color bodies from the glucosic process stream. Such conditions are dependent on a variety of factors including the specific strong acid, weak base and weak acid resins employed, the concentration of anions, cations or color bodies in the glucosic process stream and the like.

Although batch type ion-exchange techniques can be employed, in the practice of the present invention, continuous techniques wherein the glucosic process stream is continuously flowed, either upwardly or downwardly, through the resin beds comprising the individual resins are generally preferred. In general, to avoid the intermixing of the individual resins during operation or subsequent regeneration, each resin type is contained by an individual tank or column. Alternatively, two or more resins can be separately contained within a single column. For example, it is often advantageous to have the strong cation resin contained in a column followed by a column containing the separate weak base and weak acid resins. In such case, the individual weak base and weak acid resins are maintained separate and unmixed using a fluid permeable, resin impermeable plate, screen or baffle.

The relative amounts of the weak acid, strong acid and weak base resins employed and the flow rate of the glucosic process stream through the individual resins is dependent upon many factors including the capacity (i.e., the total amounts of ions which the resin can abstract from the glucosic process stream) and kinetics (i.e., the rate at which ions are abstracted from the glucosic process stream) of the individual ion-exchange resins, the composition of the glucosic process stream, the desired reduction in the concentration of anions and cations in the process stream prior to isomerization and the like. In general, in order to remove the desired amount of anions, cations and color bodies from solution, the glucosic process stream is advantageously flowed through the strong acid and weak base resins at approximately equal rates, typically varying from 0.5 to 10 volumes of the glucosic process stream per volume of resin bed (i.e., 0.5 to 10 bed volumes (BV) of the process stream) per hour. Typically, the process stream is preferably flowed through each resin bed at a rate from 1 to 5 BV per hour. Alternatively, the glucosic process stream can be flowed through the weak acid resin at rates of up to 40 BV per hour, preferably from 5 to 20, more preferably from 10 to 15, BV per hour.

Advantageously, the different resins are employed in amounts such that the individual resins become exhausted at approximately the same time. Since the desired flow rate of the glucosic process stream through each of the strong acid and weak base resins are generally approximately equal, in practice, the strong acid resin is advantageously employed in an amount from 0.8 to 1.2 equivalents for each equivalent of the weak base resin (i.e., the process stream is advantageously treated with from 0.8 to 1.2 equivalents of cationic-exchange sites for each equivalent of anionic-exchange sites) which typically corresponds to employing from 0.9 to 1.1 volumes of the strong acid resin for each 1.0 to 1.2 volumes of the weak base resin being employed. Preferably, from 0.9 to 1.1 equivalents of the strong acid resin are employed for each equivalent of the weak base resin. Most preferably, the weak base resin is employed in amounts slightly greater than the strong acid resin on an equivalent basis.

Since the flow rate of the glucosic process stream through the weak acid resin can be significantly higher than through either the proceeding strong acid or weak base resins, the weak acid resin is employed in correspondingly lesser amounts. In general, the weak acid resin will be employed in amounts from 0.05 to 0.7, preferably from 0.1 to 0.5 volume per volume of the strong acid and weak base resins.

The treatment of the glucosic process stream with the resins is normally conducted at slightly elevated temperatures, e.g., from 40° C. to 80° C. and at atmospheric or slightly greater pressures, e.g., from 1 to 5 atm (101 to 507 kPa).

Upon exhaustion of a resin, the resin is regenerated for subsequent reuse using techniques well-known in the art for regenerating the specific type of resin. In general, the weak acid and strong acid resins can be regenerated using a regenerant such as sulfuric or hydrochloric acid, generally hydrochloric acid, which exchanges H+ for the calcium, magnesium, potassium and other cations now bonded to the resin. In general, both the weak acid and strong acid resins can be regenerated using the same acid stream by passing said acid stream through the weak acid resin and subsequently through the strong acid resin.

The weak base resin is regenerated using conventionally employed regenerants such as an aqueous solution of sodium hydroxide, sodium carbonate or ammonium hydroxide. In general, ammonium or sodium hydroxide is employed as the regenerant, thereby converting the sulfate and chloride form of the weak base resin to the hydroxide form. Following regeneration, the regenerated resins are generally rinsed with deionized water to remove any of the regenerant entrapped or entrained by the resin. Using conventional techniques, after extended cycles of operation, as many as 20 to 30 BVs of rinse water are required to ensure that the entrapped or entrained sodium on the weak base resin is reduced to desirably low levels. Alternatively, using the process of the present invention, since any sodium entrapped by the weak base resin during regeneration and thereafter rinsed by the glucosic process stream will subsequently be removed from the process stream, prior to isomerization, by the weak acid resin, only 3 to 4 BVs of rinse water are generally required following regeneration. This reduction in the required amounts of rinse water reduces the non-productive period during each cycle of operation which corresponds to increased production efficiencies.

In the embodiment where the weak acid and weak acid resins are contained unmixed but in a single column, regeneration advantageously comprises passing the aqueous alkaline solution, e.g., sodium hydroxide solution, through both resins and subsequently passing the aqueous, acidic solution, e.g., hydrochloric acid solution, through the weak acid resin.

Following isomerization, the resulting glucose/fructose mixture is advantageously recovered using conventional techniques well-known in the art. Recovery of the high fructose corn syrup product generally includes a purification step wherein the glucose/fructose mixture is deashed and decolorized by sequentially contacting the mixture with a resin bed containing a second strong acid resin and then a resin bed containing a second weak base resin. Advantageously, to reduce the amounts of rinse water required following regeneration of the weak base resin used in this purification step, the glucose/fructose mixture is advantageously contacted with a weak acid resin following its purification with the strong acid and weak base resins.

Following this purification, the fructose/glucose mixture is conventionally concentrated by dewatering the mixture such as by an evaporator. In addition, the mixture is often subsequently subjected to an enrichment operation wherein the fructose concentration of the mixture is increased, preferably using a cation-exchange resin in the calcium form, said resin often being referred to as a "separation" resin and, optionally, a polishing operation wherein certain materials (e.g., silica, benzene sulfonic acid derivatives and weak acids) which can destabilize fluids in processed foods and beverages are removed using a resin bed comprising a mixture of strong acid cation and strong base anion-exchange resins.

What is claimed is:

1. An improved method for preparing high fructose corn syrup wherein a glucose-containing process stream is sequentially treated with a strong acid cation-exchange resin and then an anion-exchange resin prior to the enzyme isomerization of at least a portion of the glucose to the fructose, the improvement in said method comprising contacting the glucose-containing process stream with a weak acid resin subsequent to the treatment of the process stream with the strong acid and anion resins but prior to enzyme isomerization.

2. The method of claim 1 wherein the anion-exchange resin is a weak base resin.

3. The method of claim 2 wherein the weak acid resin is the cross-linked polymer or copolymer of acrylic or methacrylic acid.

4. The method of claim 3 wherein the weak acid resin is a macroporous type resin having a volume average particle size of 0.3 to 1.2 millimeters.

5. The method of claim 4 wherein the strong acid resin is a sulfonated copolymer resin of styrene and a cross-linking monomer of the macroporous type and the weak base resin is a secondary amine derivative of a macroporous type copolymer of styrene and cross-linking monomer.

6. The method of claim 1 wherein the fructose/glucose mixture is sequentially contacted, following enzyme isomerization, with a strong acid cation-exchange resin and strong base anion-exchange resin.

7. The method of claim 6 wherein the fructose/glucose mixture is contacted with a weak acid resin subsequent to the sequential treatment of the mixture with the strong acid and weak base resins.

8. The method of claim 7 wherein the weak acid resin is the cross-linked polymer or copolymer of acrylic or methacrylic acid.

* * * * *